June 10, 1969 F. W. ANDERSON Plant Pat. 2,894
NECTARINE TREE
Filed Nov. 13, 1967
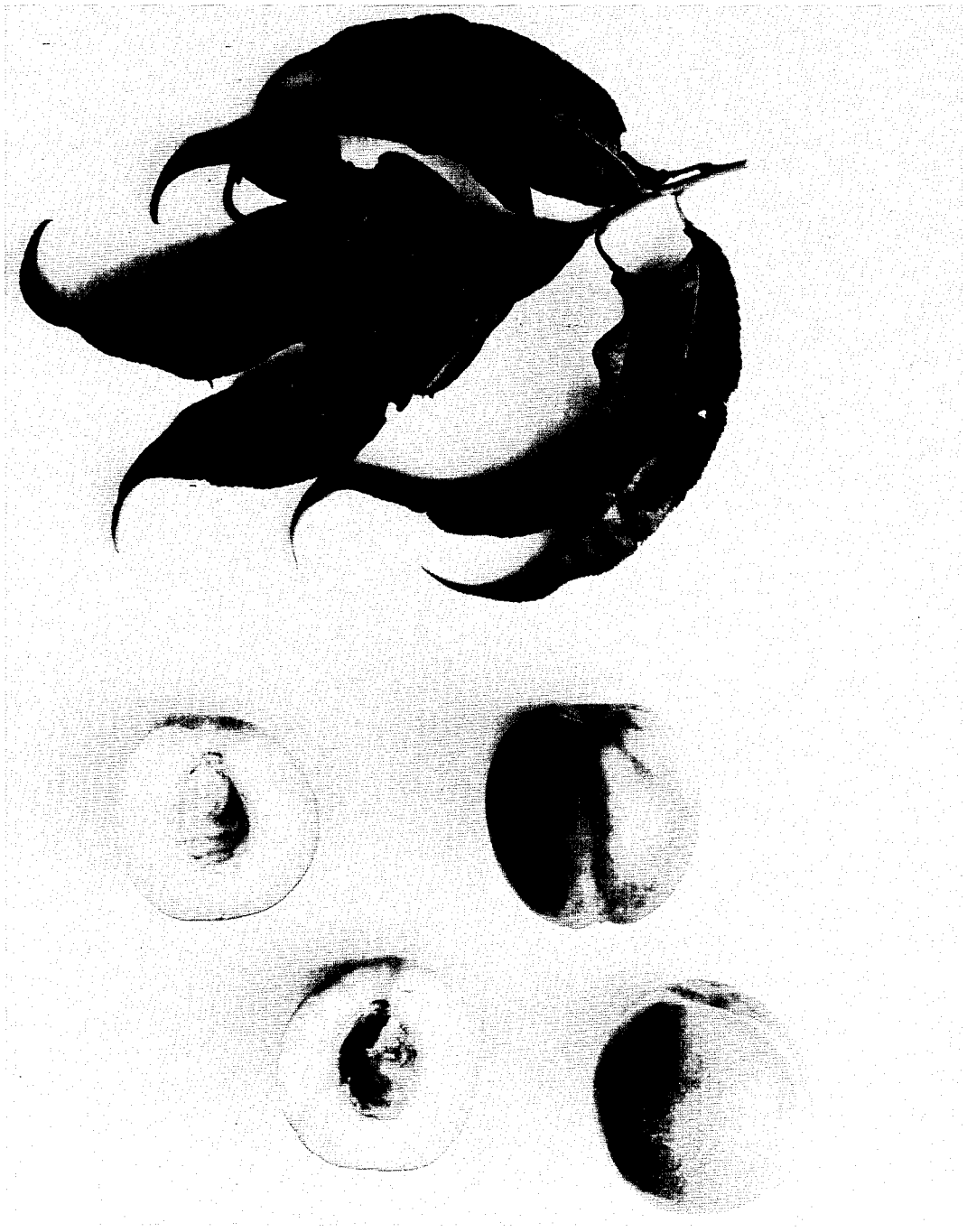
INVENTOR
Frederic W. Anderson
BY Webster & Webster
ATTORNEYS United States Patent Office Plant Pat. 2,894
Patented June 10, 1969

2,894
NECTARINE TREE

Frederic W. Anderson, Merced, Calif., assignor to Reedley Nursery, Inc., Reedley, Calif., a corporation of California Filed Nov. 13, 1967, Ser. No. 682,688
Int. Cl. A01h 5/08
U.S. Cl. Plt—41 1 Claim

ABSTRACT OF THE DISCLOSURE

A large to medium size, vigorous nectarine tree which is a regular and prodctive bearer of large, uniform, globose fruit of clingstone type; the fruit having yellow flesh, and yellow skin partially overspread with red.

*Classification of the variety*

The present variety of nectarine tree is embraced by Group 123 of the classification established by Caillavet and Souty in their Monographie des Principales Variétés de Pêchers, 1950 edition.

*Background of the variety*

Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program.

*Origin of the variety*

The present veriety of nectarine tree was originated by me, at my experimental nursely and orchard located as foresaid, as a cross between the Late Le Grand nectarine (United States Plant Patent No. 1,035) and an unnamed seedling of the Gold King nectarine (United States Plant Patent No. 1,424). One seedling of such cross, and which is the instant variety, evidenced—under continuing observation—desirable characteristics and was, therefore, selected by me for asexual reproduction, preparatory to commercialization.

*Asexual reproduction of the variety*

Subsequent to origination of the variety, as above, I asexually reproduced it by top-working on mature trees in my aforementioned orchard. In maturity, all of such reproductions ran true to the original tree in all respects.

*Summary of the variety*

The herein claimed variety of nectarine tree—which is of large to medium size, vigorous, and spreading in growth—is a regular and productive bearer of large, uniform, globose fruit having a cling stone, yellow fiesh, and yellow skin partially overspread with red; the variety being particularly characterized by a ripening period of the fruit which is slightly later than the Regal Grand (United States Plant Patent No. 1,751) and the Gold King, and in general somewhat resembles the latter.

In addition to extending the marketing period for the same general type of fruit, the herein claimed variety of nectarine tree is further characterized, in comparison to the Regal Grand and Gold King, by fruit which has better shipping qualities and longer shelf life; the fruit lacking the red suture line (which undesirably colors and ripens, and hence softens, before the remainder of the fruit) which is present in the Gold King.

*Brief description of the drawing*

The drawing is an illustration, by photographic reproduction in color, of a twig with leaves, and detached fruit; one fruit being cut in half to expose the flesh, and with the stone remaining in one cut half.

*Description of the variety*

The botanical details of this new and distinct variety of nectarine tree—with color definitions referenced to Maerz and Paul Dictionary of Color—are as follows:

Tree:
- *Size.*—Large to medium.
- *Vigor.*—Vigorous.
- *Growth.*—Spreading.
- *Production.*—Productive.
- *Bearing.*—Regular bearer.

Trunk:
- *Size.*—Medium.
- *Texture.*—Medium.

Branches: Size.—medium.

Leaves:
- *Size.*—Large. Average length—6". Average width—1¼".
- *Form.*—Lanceolate; acutely pointed.
- *Margin.*—Crenate.
- *Petiole.*—Medium length—average ⅝".
- *Glands.*—Number and position—usually 2 on petiole, and 2 to 4 on blade. Alternate; reniform.
- *Stipules.*—Absent.
- *Color.*—Top side—medium Green (23–L–8). Under side—lighter Green (22–L–4).

Flower buds:
- *Size.*—Medium.
- *Form.*—Obtuse.

Flowers:
- *Blooming period.*—Mid-season—medium, as compared with other varieties.
- *Size.*—Large.

Fruit:
- *Maturity when described.*—Hard ripe—Sept. 15, 1967.
- *Size.*—Uniform; large. Average diameter axially—2¾". Average transversely in suture plane—2¾".
- *Form.*—Uniform; globose.
- *Suture.*—Distinct to shallow; extends from base to apex with slight depression beyond pistil point.
- *Ventral surface.*—Rounded.
- *Cavity.*—Rounded. Average depth—7/16". Average breath—9/16".
- *Base.*—Rounded.
- *Apex.*—Depresed.
- *Pistil point.*—Depressed.

Skin:
- *Thickness.*—Medium.
- *Texture.*—Medium.
- *Tendency to crack.*—None.
- *Down.*—Wanting.
- *Color.*—Yellow (11–L–2) partially overspread with Red (6–L–5).

Flesh:
- *Texture.*—Firm; fine; meaty.
- *Ripens.*—Evenly.
- *Flavor.*—Subacid.
- *Aroma.*—Distinct.
- *Eating quality.*—Good.
- *Color.*—Yellow (10–L–4). Surface of pit cavity—Red (5–L–3) streaked slightly into flesh.

Stone:
- *Type.*—Cling.
- *Size.*—Medium. Average length—1⅛". Average breath—1". Average thickness—⅝".
- *Form.*—Globose to oblong.

*Base.*—Straight.
*Apex.*—Rounded.
*Sides.*—Equal.
*Ridges.*—Rounded.
*Ventral edge.*—Thick.
*Dorsal edge.*—Full.
*Tendency to split.*—Slight.
*Color.*—Garnet Red (7–J–6).

Use: Market—local. Dessert. Long distance shipping.
Keeping quality: Good.
Shipping quality: Good.

The nectarine tree and its fruit herein described may vary in slight detail due to climatic and soil conditions under which the variety may be grown; the present description being of the variety as grown in the Central Valley of California, and wherein in 1967 all fruit ripened over two weeks later than normal.

I claim:

1. A new and distinct variety of nectarine tree, substantially as illustrated and described, which is of large to medium size, vigorous and spreading in growth, and a regular and productive bearer of large, uniform, globose fruit having a clingstone, yellow flesh, and yellow skin partially overspread with red; the variety being particularly characterized, in comparison to the Regal Grand and Gold King, by a slightly later ripening period of the fruit which in general somewhat resembles said Gold King, by better shipping qualities and longer shelf life, and by an absence of the red suture line, of the Gold King, which colors and ripens before the remainder of the fruit.

No References Cited

ROBERT E. BAGWILL, *Primary Examiner.*